United States Patent
White et al.

(10) Patent No.: US 11,198,889 B2
(45) Date of Patent: Dec. 14, 2021

(54) PROCESS FOR THE MANUFACTURE OF BUTANOL OR ACETONE

(71) Applicant: Celtic Renewables Limited, Edinburgh (GB)

(72) Inventors: Jane Samantha White, Edinburgh (GB); Kenneth Alexander Leiper, Edinburgh (GB); Martin Tangney, Edinburgh (GB); Sandra Messenger, Sharnbrook (GB)

(73) Assignee: Celtic Renewables Limited, Edinburgh (GB)

( * ) Notice: Subject to any disclaimer, the term of this patent is extended or adjusted under 35 U.S.C. 154(b) by 0 days.

(21) Appl. No.: 16/792,470

(22) Filed: Feb. 17, 2020

(65) Prior Publication Data

US 2020/0181655 A1    Jun. 11, 2020

Related U.S. Application Data

(63) Continuation of application No. 16/156,335, filed on Oct. 10, 2018, now abandoned, which is a continuation of application No. 15/852,556, filed on Dec. 22, 2017, now abandoned, which is a continuation of application No. 15/407,715, filed on Jan. 17, 2017, now abandoned, which is a continuation of application No. 13/806,248, filed as application No. PCT/GB2011/051237 on Jun. 30, 2011, now abandoned.

(30) Foreign Application Priority Data

Jul. 1, 2010  (GB) ...................................... 1011079

(51) Int. Cl.
| | | |
|---|---|---|
| C12P 7/36 | (2006.01) | |
| C10L 1/02 | (2006.01) | |
| C12F 3/10 | (2006.01) | |
| C12P 7/34 | (2006.01) | |
| C12P 7/16 | (2006.01) | |
| C12P 7/28 | (2006.01) | |
| C07C 31/12 | (2006.01) | |
| C08B 1/00 | (2006.01) | |
| C12F 3/06 | (2006.01) | |

(52) U.S. Cl.
CPC ............... *C12P 7/36* (2013.01); *C07C 31/12* (2013.01); *C08B 1/003* (2013.01); *C10L 1/02* (2013.01); *C10L 1/023* (2013.01); *C12F 3/06* (2013.01); *C12F 3/10* (2013.01); *C12P 7/16* (2013.01); *C12P 7/28* (2013.01); *C12P 7/34* (2013.01); C10G 2300/1014 (2013.01); C10L 2290/26 (2013.01); Y02E 50/10 (2013.01); Y02P 30/20 (2015.11)

(58) Field of Classification Search
CPC ...... C12P 7/36; C12P 7/28; C12P 7/34; C12P 7/16; C12F 3/10
See application file for complete search history.

(56) References Cited

U.S. PATENT DOCUMENTS

| | | |
|---|---|---|
| 2009/0093027 A1 | 4/2009 | Balan et al. |
| 2010/0055236 A1 | 3/2010 | Ibarra et al. |
| 2013/0219776 A1 | 8/2013 | White et al. |
| 2013/0298453 A1 | 11/2013 | White et al. |

FOREIGN PATENT DOCUMENTS

| | | |
|---|---|---|
| EP | 0169068 A2 | 1/1986 |
| FR | 2488272 A2 | 2/1982 |
| GB | 01962 | 1/1907 |
| GB | 02591 | 1/1908 |
| GB | 00464127 A | 4/1937 |
| JP | 148801 C | 9/1941 |
| JP | 2005328801 A | 12/2005 |
| WO | WO-2007089677 A3 | 8/2007 |
| WO | WO-2010/083652 A1 | 7/2010 |

OTHER PUBLICATIONS

Kim et al. "Composition of corn dry-grind ethanol by-products: DDGS, wet cake, and thin stillage" Bioresource Technology 99 (2008) 5165-5176 (Year: 2008).*

Murakam et al. "Liquid Fuel Production From Ethanol Fermentation Stillage By Thermochemical Conversion" p. 792-803 from Research in Thermochemical Biomass Conversion, A. V. Bridgwater (ed) and J. I. Kuester (ed) 1988 (Year: 1988).*

De Kok, Ad., "International Search Report" for PCT/GB2011/051237, dated Sep. 9, 2011, 5 pages.

Ezeji, T., et al., "Fermentation of dried distillers' grains and solubles (DDGS) hydrolysates to solvents and value-added products by solventogenic clostridia", Bioresource Technology, Elsevier BV, GH, vol. 99, No. 12, Aug. 1, 2008, pp. 5232-5242.

Jones, D.T., et al., "Acetone-butanol fermentation revisited", Microbiological Reviews, American Society for Microbiology, Washington, DC, US, vol. 50, No. 4, Dec. 1, 1986, pp. 484-524.

Tshiteya, et al., "Fuel production from a brewery residue", Energy, Pergamon Press, Oxford, GB, vol. 10, No. 12, Dec. 1, 1985, pp. 1299-1306.

(Continued)

*Primary Examiner* — Thane Underdahl
(74) *Attorney, Agent, or Firm* — Winstead PC

(57) ABSTRACT

A process for the manufacture of butanol, acetone and/or other renewable chemicals is provided wherein the process utilises one or more of the group comprising by-products of the manufacture of malt whisky, such as draff, pot ale and/or spent lees, biomass substrates, such as paper, sludge from paper manufacture and spent grains from distillers and brewers, and diluents, such as water and spent liquid from other fermentations. The process comprises treating a substrate to hydrolyse it and fermenting the treated substrate at an initial pH in the range of 5.0 to 6.0. Also provided is a biofuel comprising butanol manufactured according to the process of the invention.

16 Claims, 4 Drawing Sheets

(56) References Cited

OTHER PUBLICATIONS

Tokuda, M., et al., "Methane fermentation of pot ale from a whisky distillery after enzymatic or microbial treatment", 1998, Journal of Fermentation and Bioengineering, vol. 85, No. 5, 1998, pp. 495-501.
Ure, A.M., et al., "The Detoxification of Pot Ale and Other Copper-rich Effluents by Cementation of Copper on Aluminum Metal", Journal of the Science of Food and Agriculture, vol. 33, No. 8, 1982, pp. 711-714.
Schenkman, L., "Whiskey in the car?", Science, vol. 329, Aug. 27, 2010, p. 999.
De Kok, Ad, International Search Report for PCT/GB2011 /051238, dated Sep. 9, 2011, 5 pages.
Ashboren, D., "Making better use of distillery by-products", Brewing and Distilling International 1983 Tech. Studies Div., National Council for Res. and Development, Jerusalem, Israel, vol. 13, No. 3, Mar. 1, 1983, 3 pages.
Ecofriend website, "Researchers want to produce biofuel from spent grain whisky", Aug. 27, 2007, 1 page.
Telegraph newspaper website, "Whisky by-products used to produce biofuel to power cars", Aug. 17, 2010, 1 page.
Energy Boomer website, "The beauty of bio fuel butanol", Mar. 18, 2007, 1 page.
BBC website, "Researchers brew up whisky fuel", Aug. 22, 2007, 1 page.
White, J.S. et al., "Bioconversion of brewer's spent grains to bioethanol", FEMS Yeast Res 8, 2008, 1175-1184.
Beesch, Samuel C., "A Microbiological Process Report Acetone-Butanol Fermentation of Starches," Appl Microbiol. Mar. 1953; 1(2); pp. 85-95.
Marlatt, John A., et al.; "Acetone-Butanol Fermentation Process Development and Economic Evaluation"; Biotechnology Progress, vol. 2, No. 1; Mar. 1986; pp. 23-28.
Ezeji, Thaddeus, et al.; "Production of Acetone-Butanol-Ethanol (ABE) in a Continuous Flow Bioreactor using Degermed Corn and *Clostridium beijerinckii*", Process Biochemistry, vol. 42; Jul. 8, 2006; pp. 34-39.
Putz, Jean-Marie, et al.; "Scotland: Whisky and Distilleries, How is Whisky Made?"; www.whisky-distilleries.info/Fabrication_EN.shtml; Dec. 10, 2006; 17 pages.
Pyke, Magnus; "The Manufacture of Scotch Grain Whisky"; Journal of the Institute of Brewing, vol. 71, issue 3; Oct. 10, 1964; pp. 209-218.
Komiyama, Akiko, et al.; "Production of Acetone, Butanol and Ethanol from shochu Distillery Waste by *Clostridium saccharoperbutylacetonicum* N1 -4 (ATCC 13564)"; Sci. Bull. Fac. Agr., Kyushu Univ., vol. 55, No. 2; 2001; pp. 185-191.
Sluiter, A., et al.; "Determination of Structural Carbohydrates and Lignin in Biomass: Laboratory Analytical Procedure (LAP)"; National Renewable Energy Laboratory (NREL) Technical Report NREL/TP-510-42618; Apr. 2008; 18 pages.
Wilkie, Ann C., et al.; "Stillage Characterization and Anaerobic Treatment of Ethanol Stillage from Conventional and Cellulosic Feedstocks"; Biomass and Bioenergy, vol. 19, Issue 2; Aug. 2000; pp. 63-102.
Noureddini et al. "Stagewise Dilute-Acid Pretreatment and Enzyme Hydrolysis of Distillers' Grains and Corn Fiber" Appl Biochem Biotechnol (2009) 159:553-567.

\* cited by examiner

PROCESS FOR THE MANUFACTURE OF BUTANOL OR ACETONE

CROSS-REFERENCE TO RELATED APPLICATIONS

This patent application is a continuation application of U.S. patent application Ser. No. 16/156,335, which was filed on Oct. 10, 2018. U.S. patent application Ser. No. 16/156,335 is a continuation application of U.S. patent application Ser. No. 15/852,556, which was filed on Dec. 22, 2017. U.S. patent application Ser. No. 15/852,556 is a continuation application of U.S. patent application Ser. No. 15/407,715, which was filed on Jan. 17, 2017. U.S. patent application Ser. No. 15/407,715 is a continuation application of U.S. patent application Ser. No. 13/806,248, which was filed on May 9, 2013. U.S. patent application Ser. No. 13/806,248 is a national-stage filing of International Patent Application No. PCT/GB2011/051237, which was filed on Jun. 30, 2011. U.S. Patent Application No. 16/156,335, U.S. Patent Application No. 15/852,556, U.S. Patent Application No. 15/407,715, U.S. Patent Application No. 13/806,248, and International Patent Application No. PCT/GB2011/051237 are incorporated herein by reference in their entirety for all purposes.

FIELD OF THE INVENTION

The present invention relates to a process for the manufacture of biofuels and renewable chemicals. More particularly, the invention relates to a process for the manufacture of butanol. The invention further relates to a process for the manufacture of acetone.

BACKGROUND TO THE INVENTION

In recent years, higher oil prices, depleting fuel supplies and environmental concerns have led to a renewed interest in the production of fuels from biomass ("biofuels"). Biobutanol is produced by fermentation of biomass using bacteria, typically of the genus Clostridium. In addition to butanol, these organisms also produce acetone, which is an important solvent, and ethanol so the process is often referred to as "ABE process" (Acetone/Butanol/Ethanol process). Currently used feedstocks or substrates include energy crops, such as sugar beets, sugar cane, corn grain and wheat, as well as agricultural by-products, such as straw and corn stalks. The use of biobutanol as a fuel has several advantages over the use of ethanol. However, as biobutanol production is currently more expensive than ethanol production it has not been commercialized on a large scale.

Malt whisky refers to whisky which has been produced from no grain other than malted barley. Production of malt whisky begins with malting of barley by steeping the barley in water. Malting releases enzymes that break down starches in the grain and convert them into sugars. When the desired state of germination is reached, the malted barley is dried. The dried malted barley is mashed in a mash-tun. In mashing, the enzymes that were developed during the malting process are allowed to convert or hydrolyse the barley starch into sugar. The resulting liquid which contains the sugars is referred to as wort. This is transferred to a large vessel called a washback where it is cooled and allowed to ferment to form the "wash". The residue remaining after extraction of the soluble sugars or wort is known as draff. This comprises spent barley solids or spent grains.

The wash is distilled in a copper distillation vessel or pot still known as a wash still to produce an alcohol-containing liquid distillate, known as low wines. The distillation residue or liquor remaining in the pot still after the first distillation of spirit is known as pot ale or burnt ale. The low wines are distilled for a second and sometimes a third time in spirit stills to produce raw spirit, which is matured in oak casks to produce malt whisky. The remaining liquor in the second and subsequent distillations is called spent lees.

The by-products of the manufacture of malt whisky therefore comprise draff, pot ale and spent lees. Draff contains the non-starch components of the original barley and generally represents about twenty five percent of the total malted barley added to the mash-tun. It is rich in digestible fibre and also contains concentrated protein and oil from the malted barley. It is palatable to all types of ruminant stock. Pot ale has low total solids content and contains dead yeast cells, yeast residue, soluble protein, soluble nutrients, carbohydrates and other material from the fermentation and mashing steps. It can also contain a significant amount of copper from the stills themselves. Pot ale is rich in nutrients and may be used as a feed for most ruminant stock. However, due to its high copper content, it is not suitable for sheep. Draff and pot ale are currently categorised as being of low economic value.

SUMMARY OF THE INVENTION

The inventors of the present application have developed a process for the manufacture of butanol, acetone and/or other renewable chemicals which utilises low economic value by-products of the manufacture of malt whisky, such as draff, pot ale and/or spent lees.

According to a first aspect of the present invention there is provided a process for the manufacture of butanol and/or acetone, comprising at least the steps of:

treating a substrate comprising draff, or a derivative thereof, and pot ale to hydrolyse the substrate to provide a treated substrate, said draff comprising spent grain consisting essentially of malted barley; and fermenting the treated substrate in the presence of a culture of butanol- and/or acetone-forming micro-organisms at an initial pH in the range of 5.0 to 6.0 and at a concentration of free copper ions of less than 20 μM to provide a fermented product containing butanol and/or acetone.

In further aspects, the invention extends to the use of diluents other than pot ale, such as water, spent lees and spent liquid from other fermentations.

Accordingly, according to a second aspect of the present invention there is provided a process for the manufacture of butanol and/or acetone, comprising at least the steps of:

treating a substrate comprising draff, or a derivative thereof, and a diluent to hydrolyse the substrate to provide a treated substrate, said draff comprising spent grain consisting essentially of malted barley; and fermenting the treated substrate in the presence of a culture of butanol- and/or acetone-forming micro-organisms at an initial pH in the range of 5.0 to 6.0 to provide a fermented product containing butanol and/or acetone.

In certain embodiments, the diluent is selected from the group consisting of pot ale, water, spent lees and spent liquid from other fermentations, or a combination thereof. In particular, the diluent may be water.

In further aspects, the invention extends to the use of biomass substrates other than draff. Examples of biomass substrates include, but are not limited to, municipal waste, industrial biological waste, agricultural crops and crop residues, wood and forestry waste, marine biomass and bioenergy crops. Specific examples include paper, sludge from paper manufacture, spent grains such as those derived from distillers and brewers, fruit and vegetable waste, waste from the baking industry, seaweed and seaweed extracts, wood chip and other forestry derivatives, food crops, such as grain and crop residues, chocolate, algae (macro and micro algae), non-edible crops (and residues) and energy crops, such as switchgrass.

Accordingly, according to a third aspect of the present invention there is provided a process for the manufacture of butanol and/or acetone, comprising at least the steps of:
  treating a biomass substrate, or a derivative thereof, and a diluent to hydrolyse the substrate to provide a treated substrate; and
  fermenting the treated substrate in the presence of a culture of butanol- and/or acetone-forming micro-organisms at an initial pH in the range of 5.0 to 6.0 to provide a fermented product containing butanol and/or acetone.

In certain embodiments, the substrate is paper, such as waste paper.

The diluent may be selected from the group consisting of pot ale, water, spent lees and spent liquid from other fermentations, or a combination thereof. In particular, the diluent may be pot ale.

Accordingly, according to a fourth aspect of the present invention there is provided a process for the manufacture of butanol and/or acetone, comprising at least the steps of:
  treating a biomass substrate, or a derivative thereof, and pot ale to hydrolyse the substrate to provide a treated substrate; and
  fermenting the treated substrate in the presence of a culture of butanol- and/or acetone-forming micro-organisms at an initial pH in the range of 5.0 to 6.0 and at a concentration of free copper ions of less than 20 µM to provide a fermented product containing butanol and/or acetone.

In certain embodiments, the substrate is paper, such as waste paper.

According to a further aspect of the present invention there is provided a biofuel comprising butanol and/or acetone manufactured according to the process of any of the aspects of the present invention.

According to a yet further aspect of the present invention there is provided use of one or more by-products of the production of malt whisky in the manufacture of butanol and/or acetone by fermentation. In certain embodiments, the one or more by-products of the manufacture of malt whisky comprise draff, pot ale and/or spent lees.

DETAILED DESCRIPTION OF INVENTION

Certain embodiments of the present invention utilise draff, pot ale, spent lees and/or other biomass substrates, such as waste paper. In particular, the present inventors have surprisingly discovered that it is possible to carry out fermentation in the presence of pot ale. It was expected that the high copper content in the pot ale from the copper pot stills would inhibit butanol- and/or acetone-forming micro-organisms, such as bacteria of the genus *Clostridium*. However, the present inventors have shown that when the substrate is diluted to lower the concentration of free copper ions to below 20 µM, there is no inhibitory effect, The use of pot ale in the manufacture of butanol, acetone and/or other renewable chemicals has several associated advantages. Pot ale is currently categorised as being of low economic value. The use of pot ale in the present invention allows the economic value of pot ale to be increased. Furthermore, the pot ale acts as a solvent to dissolve the substrate. Thus, the amount of water or other diluent required is reduced when pot ale is used. In addition, pot ale provides essential nutrients to the microorganisms improving the fermentation and overall conversion of substrate to products.

The use of draff spent lees and/or other biomass substrates in the manufacture of butanol, acetone and/or other renewal renewable chemicals is also advantageous as it provides a solution to the disposal of these substances. Draff, in particular, is currently categorised as being of low economic value.

In certain embodiments, the draff, pot ale and/or spent lees are by-products of the manufacture of malt whisky. The use of these by-products in the present invention thus allows low economic value by-products to be recycled and offers a unique solution to the disposal of these by-products of malt whisky production.

In certain aspects, the present invention utilises biomass substrates, such as paper, and in particular waste paper. The present invention therefore further provides a solution to the disposal of waste paper, for example, old newspapers or used photocopier paper.

The substrate must be treated to hydrolyse it, thus breaking down the substrate into a form suitable for fermentation. Accordingly, in certain embodiments the substrate is subjected to one or more treatment steps to hydrolyse it, for example, mashing, heating, addition of acid or alkali, addition of enzymes or a combination thereof. In certain embodiments, the treating of the substrate to hydrolyse it comprises the step of hydrolysing the substrate in the presence of water and hydrogen ions or water and hydroxide ions. In certain embodiments, the treating of the substrate to hydrolyse it is carried out in the presence of any suitable acid which is capable of hydrolysing the substrate. Examples of suitable acids include sulphuric acid and nitric acid. Sulphuric acid is a preferred example of an acid for use in the present invention. In certain embodiments, the treating of the substrate to hydrolyse it comprises addition of one or more enzymes, such as cellulase and hemicellulase. In certain embodiments, a combination of treatments may be utilised, for example, addition of both acid and enzymes, to provide a treated substrate in a form suitable for fermentation. The combination of treatments may be applied simultaneously or sequentially.

In certain embodiments wherein the substrate is draff and the diluent is water, the treatment may comprise addition of enzymes. In alternative embodiments wherein the substrate is draff and the diluent is pot ale, the treatment may comprise addition of acid and enzymes.

Fermentation of the treated substrate is carried out at an initial pH in the range of 5.0 to 6.0, preferably in the range of 5.3 to 5.7 and more preferably at 5.5. The use of this pH range has been shown to provide high yields of butanol and/or acetone. Furthermore, this pH range allows fermentation to be carried out without the need to remove solids therefrom, thus reducing costs and avoiding any technical problems caused by the requirement to remove solids. This pH range prevents any potential toxicity from the treated substrate while maximising butanol and/or acetone production.

Fermentation is carried out in the presence of a culture of butanol- and/or acetone-forming micro-organisms. The butanol- and/or acetone-forming micro-organisms may be selected from any solvent producing micro-organisms which are capable of fermenting the substrate to form butanol and/or acetone. Suitable micro-organisms include micro-organisms engineered to produce solvents. Examples of suitable micro-organisms include those currently used in ABE (Acetone/Butanol/Ethanol) manufacture, and, in particular, bacteria of the genus *Clostridium* such as *C. acetobutylicurn, C. beijerinckii, C. saccharoperbutylacetonicurn* and *C. saccharobutylicum*. In particular embodiments, the butanol- and/or acetone forming micro-organisms comprise *C. acetobutylicum*.

Fermentation is carried out at a concentration of free copper ions of less than 20 μM. This ensures that the presence of the copper ions have no/minimal negative effect. In certain embodiments, water or another aqueous solution may be added to lower the concentration of free copper ions to below 20 μM free copper ions. In certain embodiments, the concentration of free copper ions is less than 19, 18, 17, 16, 15, 14, 13, 12, 11, 10, 9, 8, 7, 6 or 5 μM free copper ions during at least the fermentation step, In certain embodiments, the concentration of free copper ions is less than 15 μM. In certain embodiments, the concentration of free copper ions is less than 10 μM.

In certain embodiments, the treating and fermenting steps are carried out simultaneously. This reduces the amount of time required, the number of steps involved and the associated cost of manufacture.

In alternative embodiments, the treating and fermenting steps are carried out sequentially. For example, draff may be pre-treated in two steps, first with acid and then enzyme, prior to fermentation.

In certain embodiments, the fermented product further comprises one or more of the compounds selected from the group comprising ethanol, carbon dioxide, hydrogen, acetate and butyrate. Butanol and/or acetone may be separated out of the fermented product using conventional separation techniques. Alternatively, the fermented product may be used as a fuel or otherwise without further purification.

In certain embodiments wherein draff is utilised, the spent grain consists of 100% malted barley.

In certain embodiments wherein the substrate comprises a by-product of the manufacture of malt whisky, the malt whisky is a Scotch malt whisky.

The term "biobutanol" as used herein refers to butanol made from biomass.

The term "draff" as used herein refers to the composition of spent barley solids and spent grain which remains in a mash-tun after the liquor wort) has been drawn off in the manufacture of malt whisky.

The term "pot ale" as used herein refers to the liquor remaining in the wash (copper pot) still after the first distillation in the manufacture of malt whisky. It is the residue of the wash after extraction by distillation of the low wines.

The term "spent lees" as used herein refers to the liquor remaining n the distillation vessel after second and subsequent distillations in the manufacture of malt whisky. It is the residue of the low wines after extraction by distillation of raw spirit.

The term "consisting essentially of malted barley" is understood herein to refer to substrates which contain no, or only very minimal, types of grain other than malted barley. It therefore encompasses by-products of the manufacture of malt whisky. It is intended to encompass malted barley grains containing minor impurities other than other types of grain.

The term "concentration of free copper ions" refers to the concentration of copper ions which is not bound to solids, that is, the concentration of copper ions in the supernatant. The total concentration of copper in the pot ale will be higher than the concentration of free copper ions as some copper remains bound to solids, such as dead yeast cells.

The term "Scotch whisky" as used herein refers to whisky made in Scotland. In alternative embodiments, the malt whisky is a malt whisky manufactured in other countries, such as Ireland or India, where the process for manufacture of malt whisky in that country is similar or identical to the process used in Scotland for the manufacture of Scotch malt whisky.

The present invention will now be described with reference to the following examples which are provided for the purpose of illustration and are not intended to be construed as being limiting on the present invention.

BRIEF DESCRIPTION OF THE FIGURES

FIG. 1(a) shows sugars resulting from acid and enzyme treatment, FIG. 1(b) shows residual sugars after fermentation, FIG. 1(c) shows the ABE products from fermentation and FIG. 1(d) shows yield of butanol and ABE from draff;

EXAMPLES

General Methods

Figure 1:
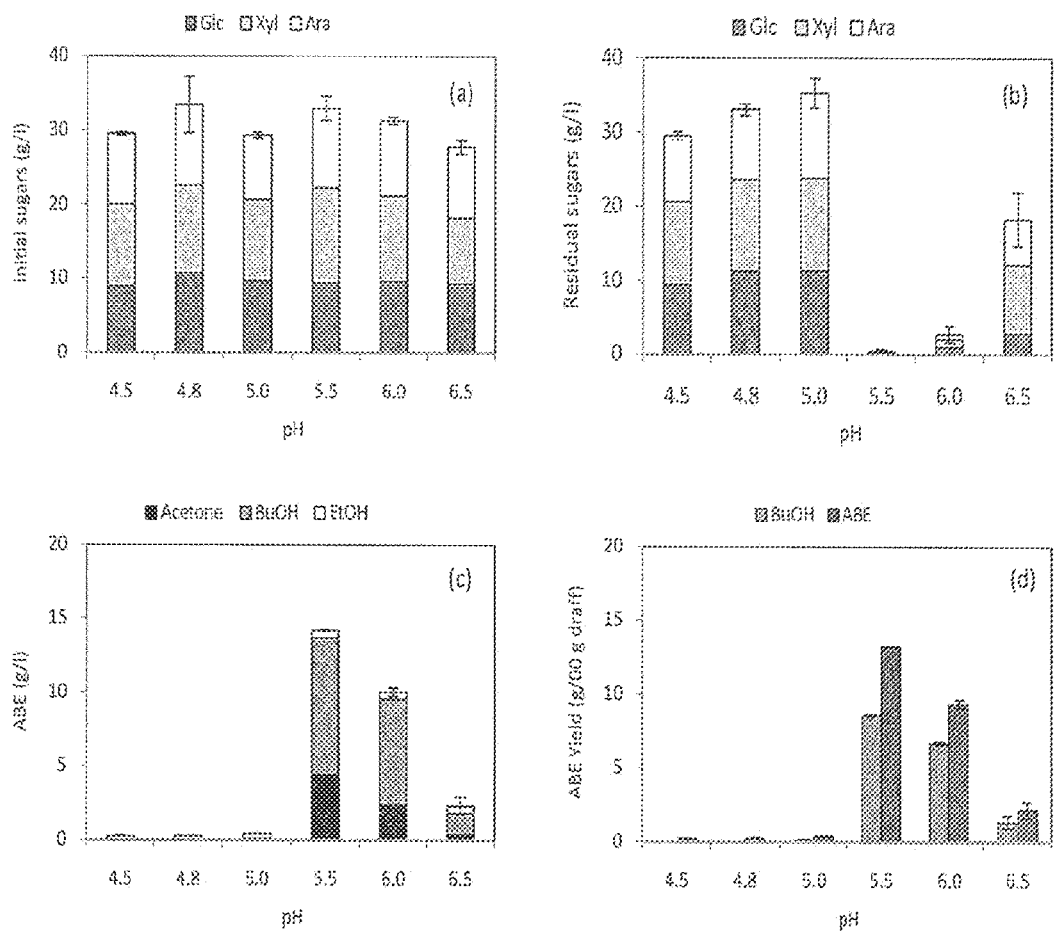
FIG. 1 shows the influence of initial pH on fermentation of acid and enzyme pre-treated draff in pot ale by *C. acetobutylicum* ATCC 824. Draff was pre-treated with 0.08 M $H_2SO_4$ and the pH adjusted to between pH 5.0-6.0 prior to enzyme addition. After enzyme hydrolysis, the pH was adjusted to 4.5, 4.8, 5.0, 5.5, 6.0 or 6.5 for fermentation.

The following organisms were used: *C. acetobutylicum* ATCC 824, *C. beijerinckii* NCIMB 8052 and *C. saccharoperbutylacetonicum* NCNB 12606. Clostridia were maintained as spore suspensions at 4° C. Spores were heat shocked at 80° C. for 10 minutes and inoculated into reinforced clostridia media (RCM, Oxoid Ltd, Cambridge, UK). Cultures were incubated for 24 hours and then sub-cultured into tryptone-yeast extract-ammonium acetate media (TYA) media containing glucose before being used as a starting culture (at 5% v/v) for all experiments. TYA consisted of (g/l) tryptone, 6; yeast extract, 2; ammonium acetate, 3; $KH_2PO_4$, 0.5; $MgSO_4 \cdot 7H_2O$, 0.3; $FeSO_4 \cdot 7H_2O$, 0.01 supplemented with 5% glucose. All clostridia cultures were incubated in an anaerobic workstation under an $N_2$—$H_2$—$CO_2$ (80:10:10) atmosphere at 33° C. For 1 L scale, fermentations were conducted in fermenters (Biostat A PILES, Sartorius Stedim Ltd, Surrey, UK). Oxygen-free conditions were achieved by sparging the media in the fermenters with oxygen-free $N_2$ for 1 hour prior to inoculation with clostridia. For all 1 L fermentations, agitation was set at 200 rpm and temperature at 33° C.

Wet draff as received from the distilleries, had a moisture content between 75-80%. Where stated, draff was dried at 80° C. to a moisture content of approximately 4% and milled prior to further processing.

Solvents (ethanol, acetone and butanol) were analysed using a Chrompack 9001 gas chromatograph equipped with a flame ionisation detector and a CP SIL 5CB column of length 10 m and diameter 0.32 mm (all Chrompack, Middelburg, Netherlands). All samples were filtered through 0.2 μm cellulose acetate syringe filters before analysis and concentrations were determined by reference ethanol, acetone and butanol standards.

For acid (acetic and butyric) and monosaccharide (glucose, xylose and arabinose) analysis, samples were filtered through 0.2 μm syringe filters and acidified with $H_2SO_4$. Samples were analysed by HPLC using a Varian 920 LC fitted with integrated UV-VIS dual wavelength and refractive index detectors (Varian Ltd., Oxford, UK). Components were separated at room temperature on a Rezex ROA Organic acid $H^+$ 8% 300×7.8 mm column (Phenomenex, Cheshire, UK) with 0.005 N $H_2SO_4$ as the mobile phase at a flowrate of 0.5 ml/min. Acids were detected at 210 nm while sugars were detected with the RI detector and concentrations were determined by reference to the corresponding standards.

EXAMPLE 1

Composition of Draff

Draff was collected from three different malt distilleries in Scotland. The monosaccharide composition of the draff was analysed according to the Laboratory Analytical Procedure developed by the National Renewable Energy Lab for the analysis of structural carbohydrates (Sluiter et al., 2008. NREL. Laboratory analytical procedure for the determination of structural carbohydrates and lignin in biomass. NREL/TP-510-42618). The results of the analysis are provided in Table 1. Glucose, xylose and arabinose were the predominant sugars, with very low levels of galactose (less than 2%) and no mannose detected. There was little variation in the sugar composition of draff from different distilleries. Based on these values, complete hydrolysis of draff (10.5% dry draff (w/v) as used in the experiments detailed below) should yield approximately 50 g/l monosaccharide.

TABLE 1

Monosaccharide composition of draff

| | Sugar (g/100 g draff) | | | |
|---|---|---|---|---|
| Source | Glucose | Xylose | Arabinose | Total |
| Distillery 1 | 20.9 ± 0.2 | 21.3 ± 0.1 | 9.0 ± 0.2 | 51.2 ± 0.2 |
| Distillery 2 | 18.4 ± 0.2 | 21.3 ± 0.2 | 9.2 ± 0.0 | 48.8 ± 0.4 |
| Distillery 3 | 20.5 ± 0.0 | 21.6 ± 0.3 | 9.3 ± 0.0 | 51.3 ± 0.3 |

EXAMPLE 2

Effect of pH control on solvent production by clostridia

The effect of pH on fermentation of glucose in TYA media by *C. acetobutylicum* ATCC 824 was investigated. Fermentations were conducted at 1 L scale and the pH was controlled at a range of set points between pH 4.5-6.5 with automated addition of either alkali or acid, At pH 4.5, no glucose utilisation, acid or ABE production was detected. For all other fermentations, glucose was completely consumed within 48 hours and acids (butyric and acetic) and solvent (acetone, butanol and ethanol) were produced (Table 2). ABE production was highest at pH 4.8 and 5.0, corresponding to yields of 0.34 and 0.30 g ABE/g sugar, respectively. Acid production increased between pH 5.5 to 6.5, with a corresponding decrease in conversion of sugar to ABE. At pH 6.5, acids only were produced with final concentrations of 7.8 and 12.8 g/l acetic and butyric acid, respectively.

TABLE 2

Conversion of 5% glucose to acid and ABE by *C. acetobutylicum* ATCC 824 in TYA media controlled at either pH 4.8, 5.0, 5.5, 6.0 or 6.5. Acid (butyric and acetic) and ABE concentrations were determined after 68 hours with ABE yield expressed as g of ABE produced per g of sugar consumed.

| pH | Acid (g/l) | ABE (g/l) | Yield (g ABE/g sugar) |
|---|---|---|---|
| 4.8 | 0.7 | 15.2 | 0.34 |
| 5.0 | 0.9 | 14.3 | 0.30 |
| 5.5 | 7.9 | 12.3 | 0.25 |
| 6.0 | 13.6 | 6.7 | 0.13 |
| 6.5 | 20.5 | 0.6 | 0.01 |

EXAMPLE 3

Pot Ale as a Growth Medium

Pot ale was collected from a Scottish malt distillery and analysed for copper content. The pot ale had 71.8 μM total Cu of which 21.1 μM was determined to be available as "free" Cu in the supernatant with the rest bound to the solids. To assess whether this Cu concentration was toxic to *C. acetobutylicum* ATCC 824, fermentation of 5% glucose in 100 ml TYA media supplemented with different concentrations of Cu was compared (Table 3). Cu had no effect on ABE production at 5 and 10 μM with ABE concentrations of approximately 12 g/l being similar to that of the control without Cu. At the higher Cu concentration, ABE concentration was reduced to 8.6 g/l, indicating that at this concentration Cu was inhibitory to clostridia. As the pot ale had a "free" Cu content of 21.1 μM, it was decided to test clostridia fermentation in half strength pot ale in order to reduce the Cu concentration below inhibitory levels. Half-strength pot ale supplemented with glucose provided enough nutrients for growth of 824 with ABE production similar to the TYA control (Table 3),

TABLE 3

Conversion of 5% glucose to ABE by *C. acetobutylicum* ATCC 824 in either TYA, TYA containing 5, 10 or 20 μM Cu or 50% pot ale.

| Media | ABE (g/l) |
|---|---|
| TYA | 12.4 ± 0.3 |
| TYA, 5 μM Cu | 12.3 ± 0.3 |
| TYA, 10 μM Cu | 11.6 ± 0.1 |
| TYA 20 μM Cu | 8.6 ± 2.0 |
| 50% pot ale | 12.0 ± 1.7 |

EXAMPLE 4

Influence of Initial pH on Fermentation of Hydrolysed Draff

The effect of initial pH on fermentation of pre-treated draff was investigated. Dried, milled draff was pre-treated by adding 10.5% (w/v) to 250 ml duran bottles with 0.08 M $H_2SO_4$ in 50% pot ale and sterilised at 121° C. for 15 min. After cooling, the pH was adjusted to between pH 5.0-6.0 by addition of 10 M NaOH and incubated with cellulase and hemicellulase enzymes at 33° C. for 24 hours. For fermentation, the pH of the solutions was adjusted to either 4.5, 4.8, 5.0, 5.5, 6.0 or 6.5 prior to inoculation with *C. acetobutylicum* ATCC 824. The initial sugar concentration was monitored before fermentation and the residual sugar, ABE concentration and ABE yield were calculated after fermentation (FIG. 1). The initial concentration of sugars was similar for all samples, with approximately 9.6, 11.2, and 9.9 g/l glucose, xylose and arabinose. No growth or gas production was apparent at pH 5.0 or lower and no sugars were utilised. ABE production was greatest at pH 5.5 (14.2 g/l) with a yield of 13.2 g/100 g draff. This was reduced at pH 6.0, with 9.3 g ABE/100 g draff At pH 6.5, approximately half the sugar was utilised but there was poor conversion to ABE with a final concentration of 2.3 g/l.

EXAMPLE 5

Fermentation of Add Pre-treated Draff in Pot Ale or Water

Figure 2:
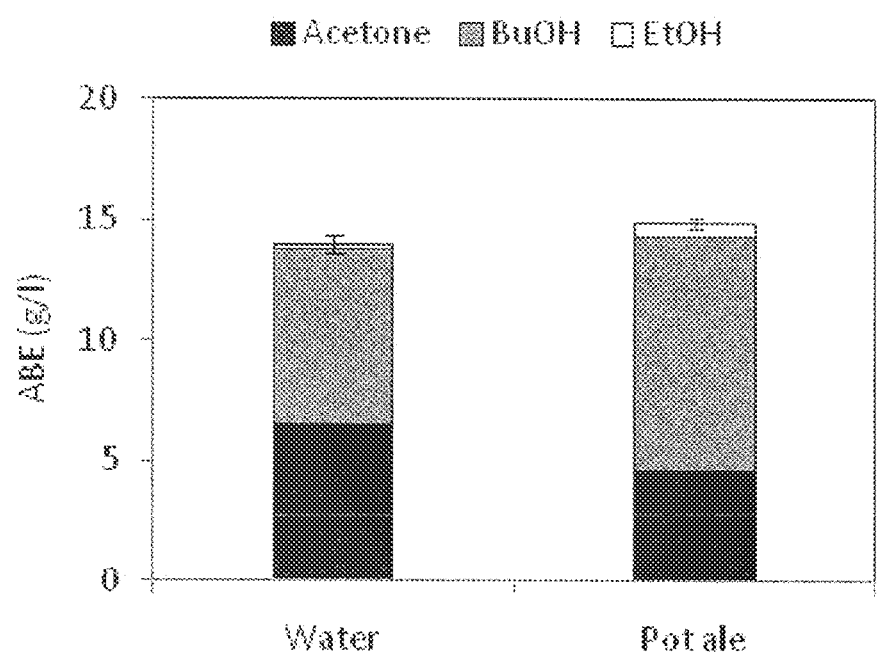
FIG. 2 compares ABE production by *C. acetobutylicum* ATCC 824 from acid-pre-treated draff in either water or pot ale. After acid treatment, the pH was adjusted to pH 5.5 and enzymes and microorganisms added.

Dried, milled draff (10.5% w/v) was pre-treated with 0.08 M $H_2SO_4$ in either water or pot ale in 250 ml duran bottles by sterilisation at 121° C. for 15 minutes. After cooling the pH was adjusted to 5.5 by the addition of 10 M NaOH, Cellulase and hemicellulase enzymes and *C. acetobutylicum* ATCC 824 inoculum were added and bottles incubated at 33° C. The ABE concentration was determined after fermentation (FIG. 2). For draff in water, ABE yield was 14.0 g ABE/100 g draff whereas in pot ale, a yield of 14.9 g ABE/100 g draff resulted.

EXAMPLE 6

Conversion of Draff to Butanol and Acetone at 1 L Scale

Figure 3:
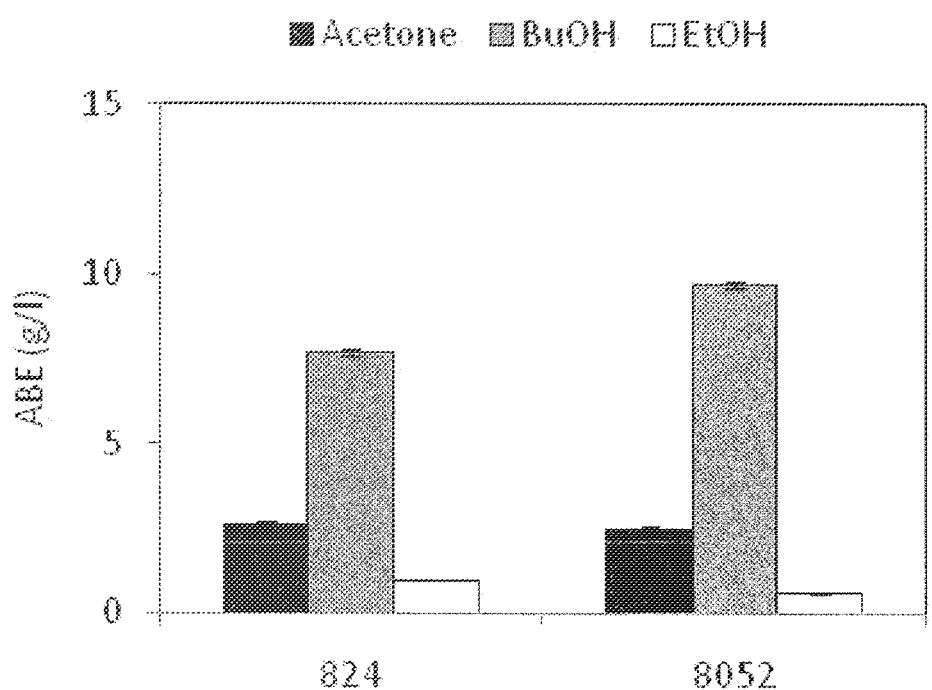
FIG. 3 shows ABE production by *C. acetobutylicum* ATCC 824 and *C. beijerinckii* NCIMB 8052 from draff at 1 L scale.

Draff (10.5% w/v) was pre-treated with 0.08 M $H_2SO_4$ in 50% pot ale in 1 L fermenters by sterilisation at 121° C. for 15 minutes. In this case draff was used wet, as received from the distillery, without any further processing. After cooling to 33° C., the pH was adjusted to pH 5.5 by the addition of 10 M NaOH and the fermenters were sparged with $N_2$. After degassing, enzymes and either 824 or 8052 were added and solvents were analysed at the end of the fermentation. Fermentation by *C. acetobutylicum* ATCC 824 and *C. beijerinckii* NCIMB 8052 resulted in ABE levels of 11.3 and 12.8 g/l, respectively (FIG. 3). This corresponded to conversion rates of 10.6 and 12.1 g ABE per 100 g draff, respectively.

EXAMPLE 7

Process for Conversion of Waste Paper to Butanol and Acetone

Figure 4:
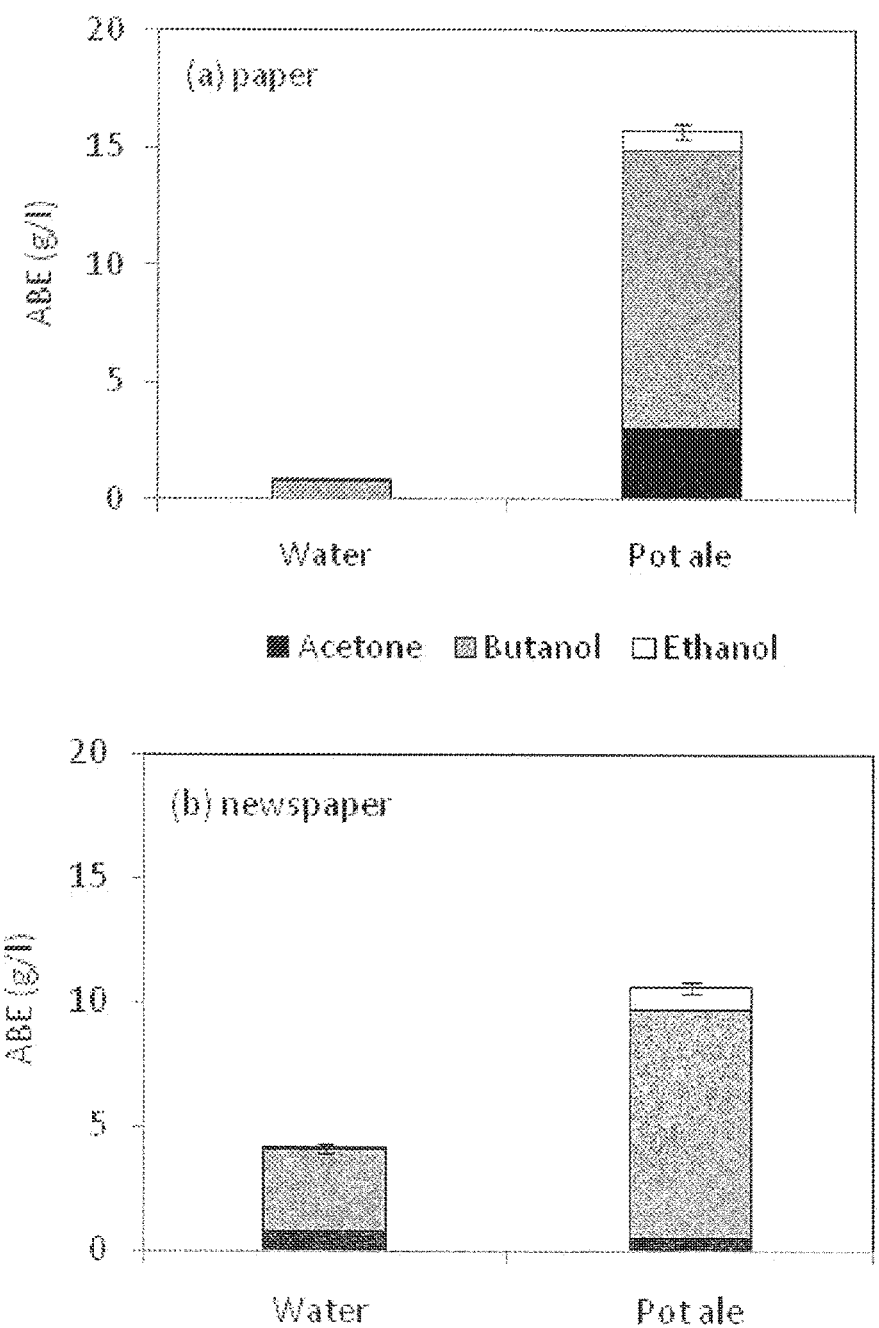
FIG. 4 shows ABE production by *C. saccharoperbutylacetonicum* NCIMB 12606 from (a) white office paper and (b) newspaper dissolved in either water or 50% pot ale.

White office paper and newspaper were shredded to 5 mm wide strips and 6.7% (w/v) was mixed with either water or 50% pot ale in 250 ml duran bottles and the pH adjusted to pH 5.5. After sterilisation, the bottles were cooled and cellulase and *C. saccharoperbutylacetonicum* NCIMB 12606 added. After fermentation, the ABE concentrations were determined (FIG. 4). There was poor conversion of paper to ABE in water compared to pot ale, demonstrating that pot ale was required to provide additional nutrients. In pot ale, the ABE yields after fermentation with *C. saccharoperbutyfacetonicum* were 24.8 g ABE per 100 g office paper and 16.8 g ABE per 100 g newspaper.

Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A process for the manufacture of butanol and/or acetone, comprising at least the steps of:
    obtaining pot ale, the pot ale being a byproduct of spirit distillation for production of malt whiskey, wherein the pot ale is a distillation residue from a copper distillation vessel comprising a distillable wash from a yeast fermentation of grain comprising malted barley;
    treating a carbohydrate substrate comprising draff, with the pot ale, to provide a treated substrate, said draff comprising spent grain consisting essentially of malted barley; and
    fermenting the treated substrate in the presence of a culture of butanol- and/or acetone-forming micro-organisms at an initial pH in the range of 5.0 to 6.0 and at a concentration of free copper ions of less than 20 µM to provide a fermented product containing butanol and/or acetone.

2. The process of claim 1, wherein the carbohydrate substrate comprises non-starch components of malted barley, said non-starch components being digestible fiber, protein and oil from the malted barley.

3. The process of claim 1, wherein the carbohydrate substrate consists essentially of draff and is treated with an acid to hydrolyze the carbohydrate substrate consisting essentially of draff.

4. The process of claim 1, wherein the carbohydrate substrate consists essentially of draff and is treated with one or more enzymes to hydrolyze the carbohydrate substrate consisting essentially of draff.

5. The process of claim 1, wherein the carbohydrate substrate consists essentially of draff and is treated with both an acid and one or more enzymes to hydrolyze the carbohydrate substrate consisting essentially of draff.

6. The process as claimed in claim 1, wherein the step of treating the substrate further comprises:
    hydrolysing the carbohydrate source in the presence of water and hydrogen ions or water and hydroxide ions.

7. The process as claimed in claim 1, wherein the step of treating the substrate further comprises:
    hydrolysing the carbohydrate source in the presence of an aqueous solution of sulphuric acid.

8. The process as claimed in claim 1, wherein the step of treating of the substrate further comprises:
    treating the carbohydrate source with one or more enzymes.

9. A process for the manufacture of butanol and/or acetone, comprising at least the steps of:
    obtaining pot ale from a malt whisky distillery, pot ale being a by-product of a first spirit distillation, wherein the pot ale is a distillation liquor residue from a copper distillation vessel containing a distillable wash from a yeast fermentation of grain comprising malted barley;

treating a carbohydrate substrate comprising draff with the pot ale, to provide a pot ale-treated carbohydrate substrate; and fermenting the pot ale-treated substrate in the presence of a culture of butanol- and/or acetone-forming microorganisms at an initial pH in the range of 5.0 to 6.0 and at a concentration of free copper ions of less than 20 µM to provide a fermentation product containing butanol and/or acetone.

10. The process of claim 9, wherein the carbohydrate substrate comprises non-starch components of malted barley, said non-starch components being digestible fiber, protein and oil from the malted barley.

11. The process of claim 9, wherein the carbohydrate substrate consists essentially of draff and is treated with an acid to hydrolyze the carbohydrate substrate consisting essentially of draff.

12. The process of claim 9, wherein the carbohydrate substrate consists essentially of draff and is treated with one or more enzymes to hydrolyze the carbohydrate substrate consisting essentially of draff.

13. The process of claim 9, wherein the carbohydrate substrate consists essentially of draff and is treated with both an acid and one or more enzymes to hydrolyze the carbohydrate substrate consisting essentially of draff.

14. The process as claimed in claim 9, wherein the step of treating the substrate further comprises:

hydrolysing the carbohydrate source in the presence of water and hydrogen ions or water and hydroxide ions.

15. The process as claimed in claim 9, wherein the step of treating the substrate further comprises:

hydrolysing the carbohydrate source in the presence of an aqueous solution of sulphuric acid.

16. The process as claimed in claim 9, wherein the step of treating of the substrate further comprises:

treating the carbohydrate source with one or more enzymes.

* * * * *